US011751587B2

(12) United States Patent
Kaatz et al.

(10) Patent No.: US 11,751,587 B2
(45) Date of Patent: Sep. 12, 2023

(54) TUNNEL PASTEURISER AND METHOD FOR OPERATING A TUNNEL PASTEURISER

(71) Applicant: KRONES AG, Neutraubling (DE)

(72) Inventors: Stefan Kaatz, Neutraubling (DE); Martin Nissen, Neutraubling (DE); Falko Jens Wagner, Neutraubling (DE)

(73) Assignee: KRONES AG, Neutraubling (DE)

( * ) Notice: Subject to any disclaimer, the term of this patent is extended or adjusted under 35 U.S.C. 154(b) by 532 days.

(21) Appl. No.: 16/764,815

(22) PCT Filed: Jul. 26, 2018

(86) PCT No.: PCT/EP2018/070361
§ 371 (c)(1),
(2) Date: May 15, 2020

(87) PCT Pub. No.: WO2019/096452
PCT Pub. Date: May 23, 2019

(65) Prior Publication Data
US 2020/0352197 A1 Nov. 12, 2020

(30) Foreign Application Priority Data
Nov. 16, 2017 (DE) ...................... 10 2017 220 471.0

(51) Int. Cl.
*A23L 3/00* (2006.01)
*A23L 3/04* (2006.01)
(Continued)

(52) U.S. Cl.
CPC ............... *A23L 3/003* (2013.01); *A23L 3/001* (2013.01); *A23L 3/04* (2013.01); *A61L 2/04* (2013.01);
(Continued)

(58) Field of Classification Search
CPC ............... A61L 2/24; A23L 3/003; A23L 3/04
See application file for complete search history.

(56) References Cited

U.S. PATENT DOCUMENTS

2009/0117237 A1   5/2009   Hansen et al.
2014/0065014 A1   3/2014   Solfa

FOREIGN PATENT DOCUMENTS

DE        3637661 A1    5/1987
DE       10310047 A1    9/2004
(Continued)

OTHER PUBLICATIONS

Zufall, C. et al., "The Biological Impact of Flash Pasteurization Over a Wide Temperature Interval," Journal of the Institute of Brewing, vol. 106, No. 3, May 2000, 6 pages.
ISA European Patent Office, International Search Repod Issued in Application No. PCT/EP2018/070361, dated Oct. 11, 2018, WIPO, 5 pages.
Del Vecchio, H. et al., "Thermal Death Time Studies on Beer Spoilage Organisms," Proceedings of the Annual Meeting of the American Society of Brewing Chemists, vol. 9, No. 1, Available as Early as Jan. 1951, 1 page.

(Continued)

*Primary Examiner* — Kevin Joyner
(74) *Attorney, Agent, or Firm* — McCoy Russell LLP

(57) ABSTRACT

Method for operating a tunnel pasteuriser with a plurality of sequentially successive treatment zones, wherein containers with a product packed therein are transported by means of a conveying device through the treatment zones and are heated with treatment media having different actual media temperatures, are pasteurized and preferably then cooled again, wherein the actual media temperatures are detected by a control unit and compared with target media temperatures, and wherein heating and/or cooling devices are controlled based on the comparison, characterised in that during the (Continued)

treatment of the containers, initial values for an optimisation are formed from the actual media temperatures of the treatment zones, and the target media temperatures are determined by means of a prediction model for determining the expected degree of pasteurisation with the optimisation, such that at least a minimum degree of pasteurisation of the containers is achieved.

14 Claims, 2 Drawing Sheets

(51) Int. Cl.
*A61L 2/24* (2006.01)
*A61L 2/04* (2006.01)
(52) U.S. Cl.
CPC ............. *A61L 2/24* (2013.01); *A61L 2202/14* (2013.01); *A61L 2202/23* (2013.01)

(56) References Cited

FOREIGN PATENT DOCUMENTS

| DE | 102005042783 A1 | 3/2007 | |
|---|---|---|---|
| EP | 1921931 B1 | 5/2008 | |
| EP | 1972210 A1 * | 9/2008 | ............. A23L 3/003 |
| EP | 2702879 A1 | 3/2014 | |
| WO | 2010094487 A1 | 8/2010 | |

OTHER PUBLICATIONS

Zufall, C. et al., "The Biological Impact of Flash Pasteurization Over a Wide Temperature Interval," The Biological Impact of Flash Pasteurization, vol. 106, No. 3, May 2000, 6 pages.

Howard, A., "Fermented Beverage Production," Second Edition, Springer US, 2003, 2 pages.

* cited by examiner

TUNNEL PASTEURISER AND METHOD FOR OPERATING A TUNNEL PASTEURISER

CROSS-REFERENCE TO RELATED APPLICATIONS

The present application is a U.S. National Phase of International Patent Application Serial No. PCT/EP2018/070361 entitled "TUNNEL PASTEURISER AND METHOD FOR OPERATING A TUNNEL PASTEURISER," filed on Jul. 26, 2018. International Patent Application Serial No. PCT/EP2018/070361 claims priority to German Patent Application No. 10 2017 220 471.0 filed on Nov. 16, 2017. The entire contents of each of the above-referenced applications are hereby incorporated by reference for all purposes.

TECHNICAL FIELD

The invention refers to a method for operating a tunnel pasteuriser and a tunnel pasteuriser.

BACKGROUND AND SUMMARY

Well known are tunnel pasteurisers in which containers with a product packed in them are pasteurised. The containers are transported by a conveying device through a plurality of sequentially successive treatment zones and heated and preferably cooled again by treatment media of different temperatures. For a suitable pasteurisation, it is important that the products are kept at a sufficiently high temperature for a sufficiently long time to ensure a minimum pasteurisation in which good germ elimination is achieved.

For this purpose, different media temperatures are set in the treatment zones, with which the temperature of the containers can be slowly raised and then preferably slowly lowered again. In order not to influence the taste of beverages or other food products too much, it is also important to prevent over-pasteurisation.

Consequently, precise control of the media temperatures with a control unit is necessary. The actual media temperatures are detected with the control unit and compared with the target media temperatures. In case of a deviation, heating and/or cooling devices for the treatment media are controlled in such a way that the target media temperatures are maintained as accurately as possible.

For example, DE 10 2005 042 783 A1 discloses a method for controlling the water temperature for the water that is dispensed for pasteurisation onto products, whereby the heat transfer into the products is taken into account for controlling the water temperature.

However, it has been found that the known controls occasionally cause undesirable oscillations between the treatment zones, which prevent uniform treatment. This can lead to a reduction in product quality.

The present invention is therefore based on the object of providing a tunnel pasteuriser and a method for operating a tunnel pasteuriser in which the treatment of the containers is more uniform, the product quality is improved and the consumption of energy and resources is reduced.

To solve this object, the invention provides a method for operating a tunnel pasteuriser.

In that, during the treatment of the containers, initial values for the optimisation are formed from the actual media temperatures of the treatment zones and the target media temperatures are determined by means of the prediction model with the optimisation such that at least a minimum degree of pasteurisation of the containers is achieved, the target media temperatures are coupled with one another via the optimisation. Consequently, the treatment zones are controlled at once by the optimisation running during the treatment, so that oscillations are avoided. As a result, the containers are treated more uniformly during transport through the treatment zones, so that the product quality is improved.

The tunnel pasteuriser can be installed in a beverage processing plant. In particular, the tunnel pasteuriser can pasteurise the product filled into the container. "Pasteurisation" here can mean that the product is heated in such a way that any germs it may contain are killed. Preferably, the tunnel pasteuriser may be placed downstream of a filling line for filling the product into the containers and/or downstream of a capper for closing the containers.

The tunnel pasteuriser can be used to pasteurise containers such as bottles, preserves, tins and/or other containers. The containers can be designed to hold gaseous, liquid, solid and/or pasty products. The products can be beverages, hygiene products, pastes, chemical, biological and/or pharmaceutical products. The containers may be fitted with a closure to hermetically seal the product inside from the environment.

The transport device may include a conveyor belt to transport the containers through the treatment zones. The conveyor belt may be provided with openings or may be of a net-like design to allow the treatment medium draining from the containers to pass through to a drain.

In the treatment zones, the containers can be overflown with treatment media, especially with water. Preferably, the containers can in a first part of the treatment zones be overflown with at least one warm treatment medium and heated. Subsequently, in a second part of the treatment zones, the containers can be covered with at least one cold treatment medium and cooled down.

The "actual media temperatures of the treatment zones" may refer to the temperature of the treatment medium in a treatment zone during operation, preferably in a line section before it exits nozzles for overflowing the containers. "Target media temperatures" can mean default values for the media temperatures stored in a storage unit of the control unit.

In the individual treatment zones, the actual media temperatures can be detected with at least one temperature sensor each and transmitted to the control unit. The control unit can be connected to the heating and/or cooling devices in order to control them.

The control unit may include a microprocessor, a storage unit, one or more analogue and/or digital interfaces and/or a display unit. A machine controller may be or include the control unit. The control unit may be adapted to carry out at least partially the method for operating the tunnel pasteuriser. For this purpose, the method for operating the tunnel pasteuriser may be stored at least partially as a computer program product in the storage unit or on a data carrier.

Here, optimisation can mean a universal optimisation algorithm known per se, which is preferably implemented in the control unit. During optimisation, a quality function can be minimised or maximised, which preferably determines a deviation of the expected degree of pasteurisation from the minimum degree of pasteurisation from the media temperatures, whereby the deviation is then minimised or maximised. The quality function can also take into account the prediction model for the degree of pasteurisation and/or the second prediction model for the energy and/or resource consumption.

The prediction model can determine, preferably calculate from the media temperatures as input the expected degree of pasteurisation as output.

The degree of pasteurisation can mean a number of pasteurisation units (PU). It can also be a period of time during which the product in the tunnel pasteuriser containers is heated above a temperature threshold. The temperature threshold can be in the range of 45° C.-90° C. and/or be set by an operator.

The minimum degree of pasteurisation may be defined as the degree of pasteurisation at which a desired minimum quality of product is achieved in the containers. It can also mean that a predetermined number of germs in the product is not exceeded. The minimum degree of pasteurisation can be a minimum period of time during which the product in the tunnel pasteuriser is heated above the temperature threshold.

"During the treatment of the containers" can mean here that the formation of the initial values and the optimisation itself are carried out simultaneously with the treatment of the containers. This can also mean that during the treatment a loop is continuously processed in which the initial values are formed from the (current) actual media temperatures and the optimisation is carried out in order to determine the (new) target media temperatures. In this way, the target media temperatures can be continuously determined as the current default values for the control system.

Optimisation can take place simultaneously over at least two of the treatment zones. In this way, temperature oscillations between the at least two treatment zones can be avoided and the products packed in the containers can be treated particularly uniformly. It is conceivable that the optimisation takes place over exactly two of the treatment zones or over all of the treatment zones simultaneously.

Preferably, a momentary degree of pasteurisation per container row can be determined preferably orthogonal to the running direction and then summed up to determine the expected degree of pasteurisation. In this way, the degree of pasteurisation can be determined with a particularly simple prediction model without high computing effort. In other words, the degree of pasteurisation can first be determined individually as the momentary degree of pasteurisation for each treatment point in a row of containers. Then the momentary degrees of pasteurisation can be summed up or integrated. It is therefore conceivable that the momentary degree of pasteurisation per container row can be determined for several treatment times within a treatment period and then added up over the treatment period.

It is advantageous to determine the momentary degree of pasteurisation per container row for the treatment zones, taking into account the media temperature of the treatment zone and at least one heat transfer parameter of the treatment medium to the container. This allows the degree of pasteurisation to be determined even more easily and with particularly low computing effort. As the treatment medium is sprayed onto the containers, for example, it usually has a different temperature than the product itself. The at least one heat transfer parameter may be designed to take into account, from one or more media temperatures of the treatment medium/media, the temperature of the containers treated with it and/or the product contained therein. The at least one heat transfer parameter may be a function or a characteristic diagram.

When optimising the target media temperatures, the actual media temperatures can be permuted by at least one change value and thus a gradient of the expected degree of pasteurisation can be determined using the prediction model. Since the optimisation works more efficiently by considering a gradient, computing power can be saved during the optimisation. "Permuted" here can mean that the actual media temperatures are changed by the change value to determine the gradient. The change value can be a small value compared to the media temperature. The change value can be in a range from −5° C. to +5° C., preferably in a range from −0.5° C. to +0.5° C. When determining the gradient, the prediction model can be called up several times with the actual media temperatures changed by means of the change values, so that the gradient can be determined from the degree of pasteurisation changed by this. Alternatively, a gradient can also be determined analytically by transforming the mathematical models, which further minimises the computing effort.

The target media temperatures can be optimised in such a way that a maximum product temperature is not exceeded. This prevents over-pasteurisation of the containers. The maximum product temperature can be determined with the prediction model, preferably using at least one heat transfer parameter. The maximum product temperature can be a temperature above which the product is reduced in taste. For example, the maximum product temperature can be in the range 61° C.-67° C.

The target media temperatures can be optimised in such a way that a maximum temperature jump between two adjacent treatment zones is not exceeded. This results in a particularly uniform product treatment. The maximum temperature jump can be a difference between the media temperatures of two adjacent treatment zones and/or be in a range of 0° C.-25° C., preferably 0° C.-20° C. It can also be a difference between a first product temperature in a first treatment zone and a second product temperature in a second treatment zone adjacent to the first.

The target media temperatures can be optimised in such a way that a maximum consumption of energy and/or resources is not exceeded and/or minimised when treating the containers. Thus an increased energy and/or resource consumption can be avoided when starting or stopping the tunnel pasteuriser. In the event of a stop, the media temperatures in the pasteurisation zones must be reduced to prevent over-pasteurisation of the products. When restarting after the stop, the media temperature in the pasteurisation zones is then increased again. It is conceivable that a slightly higher degree of pasteurisation of the containers is accepted by the optimisation in favour of energy and/or resource consumption. "Energy and/or resource consumption" can mean the consumption of the heating and/or cooling devices. The energy consumption can be energy for heating and/or cooling the containers. Resource consumption may be water consumption, for example fresh water or cooling water.

Preferably, a second prediction model can be used to determine and minimise an expected energy and/or resource consumption from the target media temperatures and compare it with the maximum energy and/or resource consumption. This makes it particularly easy to determine the energy and/or resource consumption on the basis of the media temperatures during optimisation.

Preferably, the energy and/or resource consumption can be determined per zone or per row of containers and then summed up. In this way, the energy and/or resource consumption can be determined with a particularly simple prediction model without high computing effort. In other words, the energy and/or resource consumption for each treatment zone or container row can first be determined individually as zone consumption or container row consumption. Afterwards, the zone consumptions or container row consumptions can be summed up or integrated. In the following, the calculation methods are explained on the basis of zone consumption. The calculation using the container row consumption is carried out in the same way.

It is advantageous to determine a zone consumption and/or a container row consumption for each of the treatment zones, taking into account the corresponding media temperature, at least one heat transfer parameter of the treatment medium to the containers and the heat capacity of the containers. Thus the energy and/or resource consumption can be determined even more easily and with particularly low computing effort. The at least one heat transfer parameter can be the at least one heat transfer parameter described above in relation to the degree of pasteurisation. For example, the media temperature and the heat transfer parameter can be used to determine the temperature of the container or the product packed in it. The temperature of the container can then be used to determine the heating or cooling of the product packed in the container in the corresponding treatment zone, and the mass and heat capacity of the product can then be used to determine the energy and/or resource consumption. In addition, the heat capacity and the mass of the container can be taken into account for determining the consumption of energy and/or resources.

Preferably, the target media temperatures can be optimised in such a way that a TAT value (time above temperature) and/or a KP value (killing point temperature) and/or one or more PE values (pasteurisation units) are not exceeded. With the TAT value, the minimum degree of pasteurisation is particularly easy to determine. In addition, the KP value ensures that pasteurisation is carried out at a temperature above which germ elimination takes place. Since it is also possible to introduce pasteurisation units (PE units) into the packed product at lower temperatures, the KP temperature can be used to ensure sufficient germ elimination.

In addition, the invention provides a tunnel pasteuriser.

In that the control unit is adapted to form initial values for the optimisation from the actual media temperatures of the treatment zones during the treatment of the containers and to determine the target media temperatures with the optimisation by means of the prediction model in such a way that at least a minimum degree of pasteurisation of the containers is achieved, the target media temperatures are coupled to one another via the optimisation. Consequently, the treatment zones are controlled at once by the optimisation running during the treatment, so that oscillations are avoided. Consequently, the containers are treated more uniformly during transport through the treatment zones, so that the product quality is improved.

The control unit may be designed to carry out the above described method of operating the tunnel pasteuriser.

The tunnel pasteuriser or the control unit may comprise the features described above in relation to the method of operating the tunnel pasteuriser, either singly or in any combination.

BRIEF DESCRIPTION OF THE FIGURES

Further features and advantages of the invention are explained in more detail using the following embodiments.

DETAILED DESCRIPTION

Figure 1:
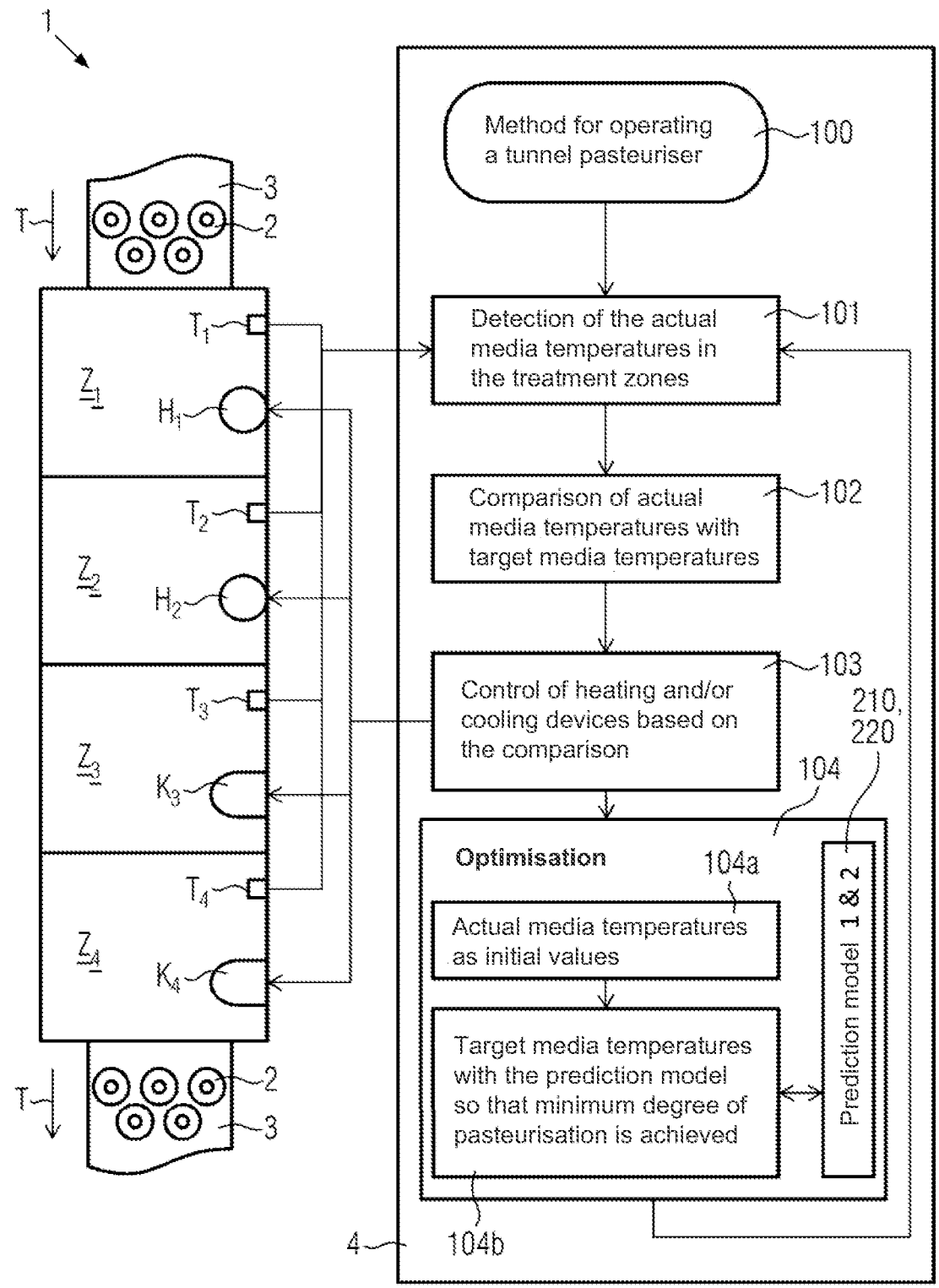
FIG. 1 shows embodiments of a tunnel pasteuriser and a method for operating the tunnel pasteuriser in a top view or as a flowchart.

FIG. 1 shows embodiments of the tunnel pasteuriser 1 and the method 100 for operating the tunnel pasteuriser in a top view or as a flowchart.

The left part of FIG. 1 shows the tunnel pasteuriser 1 with a plurality of sequentially successive treatment zones $Z_1$-$Z_4$, through which the containers 2 are transported by the conveyor device 3 in the direction T. The conveyor device 3 is here designed as a conveyor belt, for example, but can also be designed as any other suitable conveyor device. A product has been packed into the containers 2, which is pasteurised by the tunnel pasteuriser 1.

During transport through the treatment zones $Z_1$-$Z_2$, the containers 2 are sprayed with heated treatment media (water), the media temperature in the treatment zone $Z_2$ being higher than in the treatment zone $Z_1$. As a result, the containers 2 are heated step by step and kept above a minimum temperature of 60° C. for at least 10 minutes. This kills off germs in container 2 and pasteurises the product. The heating devices $H_1$, $H_2$ are provided to heat the treatment media in the treatment zones $Z_1$-$Z_2$. These can include a heater, heat exchanger and the like.

Subsequently, the containers 2 are transported through the treatment zones $Z_3$-$Z_4$ and cooled down again step by step. For this purpose, the containers 2 are each sprayed with a cool treatment medium (water), whereby the media temperature in the treatment zone $Z_4$ is lower than in the treatment zone $Z_3$. In this way the containers 2 are cooled down in a controlled and slow manner so that they can then be transported to further treatment stations after tunnel pasteuriser 1. Cooling devices $K_3$ and $K_4$ are provided to cool the treatment media in treatment zones $Z_3$-$Z_4$. These can include a controlled fresh water supply, cooling devices, heat exchangers and the like.

Furthermore, the temperature sensors $T_1$-$T_4$ are provided in the treatment zones $Z_1$-$Z_4$ to detect the respective actual media temperatures.

The heating and cooling devices $H_1$, $H_2$, $K_3$, $K_4$ as well as the temperature sensors $T_1$-$T_4$ are connected to the control unit 4 via suitable connecting lines.

On the right side of FIG. 1 one can see the control unit 4 in which the method 100 for operating the tunnel pasteuriser 1 is carried out as follows:

In step 101, the actual media temperatures of the individual treatment zones $Z_1$-$Z_4$ measured with the temperature sensors $T_1$-$T_4$ are detected, for example by means of an interface that detects an analogue or digital signal from the temperature sensors $T_1$-$T_4$. The actual media temperatures are then stored in a storage unit of the control unit 4 not shown here.

In step 102, the actual media temperatures are compared with target media temperatures also stored in the storage unit, whereby a difference is formed from the target media temperatures and the actual media temperatures.

In step 103, the heating and cooling devices $H_1$, $H_2$, $K_3$, $K_4$ are then controlled via the comparison so that the actual media temperatures correspond as closely as possible to the target media temperatures. Control signals are transmitted via the connecting lines to the heating and cooling devices $H_1$, $H_2$, $K_3$, $K_4$ and the heating or cooling capacity is corrected so that the target media temperatures are maintained as accurately as possible.

In step 104, during the treatment of the containers 2, the target medium temperatures are adjusted with an optimisation as follows:

First, in step 104a, initial values for the optimisation are formed from the actual media temperatures. In other words, the actual media temperatures are set as the start value for the optimisation.

In step 104b the expected degree of pasteurisation is calculated from the initial values and the prediction model 210 described below in relation to FIG. 2. Optionally, the expected energy and/or resource consumption is calculated from the initial values using the prediction model 220 described below in relation to FIG. 3.

Furthermore, the actual media temperatures (the temperatures of the treatment zones) or the initial values are permuted by a slight change value, for example by 0.5° C., and are also entered into the prediction model 210 or 220. In this way, changes in the degree of pasteurisation or in the energy and/or resource consumption are determined by the media temperatures to which the change value is applied, and the gradients of the degree of pasteurisation or of the energy and/or resource consumption are formed from this.

In addition, quality criteria pre-selected by the operating personnel are stored in the control unit 4. These are the minimum degree of pasteurisation and optionally a maximum product temperature, a maximum temperature jump between two adjacent treatment zones $Z_1$-$Z_4$, a maximum energy and/or resource consumption. The minimum degree of pasteurisation can be specified in the form of one or more pasteurisation units (PE), a TAT value, a KP value or a combination of these calculation methods.

Using the initial values, the gradients of the degree of pasteurisation or the energy and/or resource consumption and the quality criteria, the target media temperatures are then optimised by means of a generally known optimisation algorithm in such a way that the aforementioned quality criteria are achieved as well as possible.

Subsequently, the target media temperatures determined in this way are stored in control unit 4 and, based on this, steps 101-104 are carried out again, including the optimisation of the target media temperatures. In other words, steps 101-104 are repeated continuously during the treatment of containers 2 with tunnel pasteuriser 1. It is also conceivable that steps 101-103 and step 104 are carried out in parallel.

In that, during the treatment of container 2, initial values for optimisation 104 are formed from the actual media temperatures, the treatment zones $Z_1$-$Z_4$ and the target media temperatures are determined with the optimisation by means of the prediction model 210 in such a way that at least a minimum degree of pasteurisation of container 2 is achieved, the target media temperatures are coupled with one another via the optimisation. Consequently, the treatment zones $Z_1$-$Z_4$ are controlled at once by the optimisation 104 running during the treatment, so that oscillations are avoided. Consequently, the containers 2 are treated more uniformly during transport through the treatment zones $Z_1$-$Z_4$, so that the product quality is improved.

In addition, the optional quality criteria prevent over-pasteurisation, uneven pasteurisation due to a temperature jump, high energy and/or resource consumption, and a treatment temperature that is too low. As a result, container 2 is pasteurised in such a way that the quality of the products packed in it is particularly high and contamination with non-destroyed germs is avoided.

Figure 2:
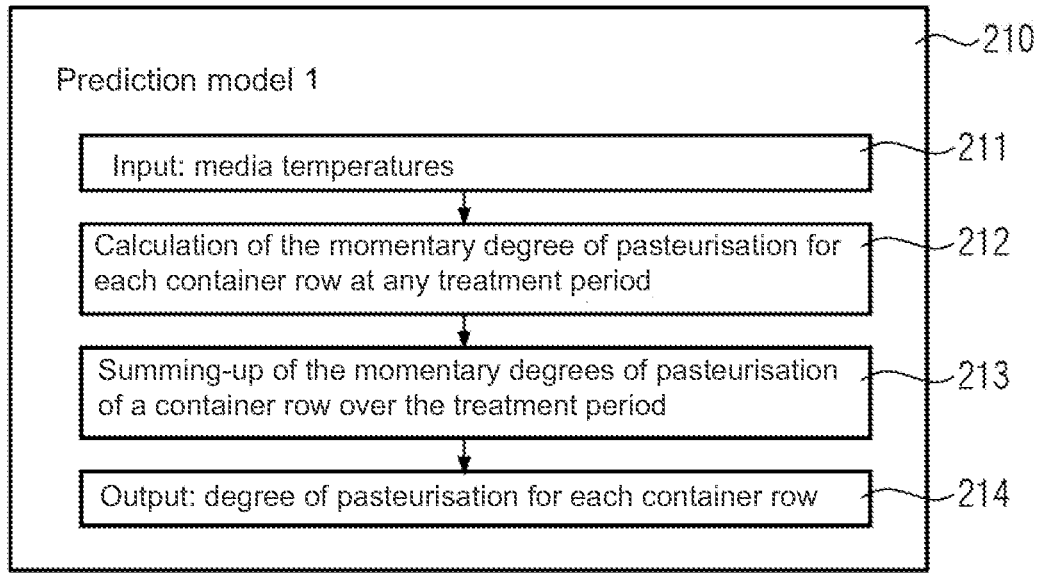
FIG. 2 shows an embodiment of a first prediction model for determining the degree of pasteurisation as a flowchart for the method from FIG. 1.

FIG. 2 shows the prediction model 210 for determining the degree of pasteurisation in a flowchart. It can be seen that a media temperature is entered into the prediction model 210 in step 211 for each of the treatment zones $Z_1$-$Z_4$.

For each of the treatment zones $Z_1$-$Z_4$, the product temperature prevailing in container 2 is now determined in step 212 by means of at least one heat transfer parameter. The at least one heat transfer parameter is preferably determined experimentally by means of a measurement, for example by spraying a container in a test chamber with a treatment medium in predetermined temperature steps and measuring the product temperature in the container for each temperature step. Calculation methods are also conceivable.

Subsequently, for each treatment zone $Z_1$-$Z_4$, the product temperature is used to determine the momentary degree of pasteurisation for each row of containers at each treatment time, for example the input to pasteurisation units (PE), which can be determined using methods generally known in the technical literature (for example in H. W. Del Vecchio, C. A. Dayharsh, and F. C. Baselt: Thermal death time studies on beer spoilage organisms. Proceedings of the American Society of Brewing Chemists, 1951, page 45; Andrew Geoffrey Howard Lea and John R. Piggott, editors: Fermented Beverage Production. Second edition. Springer, 2003. page 379; Carsten Zufall, Karl Wackerbauer: The Biological Impact of Flash Pasteurisation Over a Wide Temperature Interval, Journal of The Institute of Brewing Volume 106, Issue 3 (pages 164-168)).

Then, for each container row, the momentary degrees of pasteurisation of a container row are summed up over the treatment period in step 213 and output as degree of pasteurisation in step 214.

Figure 3:
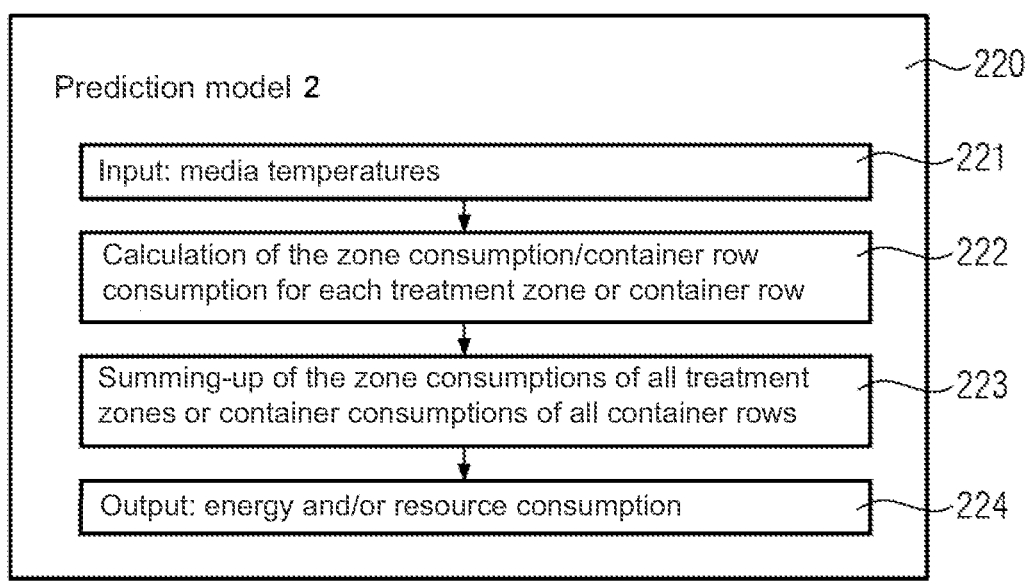
FIG. 3 shows an embodiment of a second prediction model for determining the energy and/or resource consumption as a flowchart for the method from FIG. 1.

FIG. 3 shows the prediction model 220 for determining energy and resource consumption in a flowchart. It can be seen that in step 221 a media temperature and a current product temperature are entered into the prediction model 220 for the treatment zones $Z_1$-$Z_4$.

For each of the treatment zones $Z_1$-$Z_4$, the product temperature prevailing in the containers 2 due to spraying with the treatment medium is now determined in step 222 by means of the at least one heat transfer parameter described above in relation to step 212.

Furthermore, the differential temperature by which the product is heated or cooled as it passes through the respective treatment zones $Z_1$-$Z_4$ is determined. The heat capacity of the product packed in container 2, the mass of product filled and the differential temperature can then be used to calculate the energy absorbed or released by container 2. As the number of containers in the respective treatment zone $Z_1$-$Z_4$ is known, for example by means of a counting device at the entrance of the tunnel pasteuriser 1, the zone consumption required for treatment in the treatment zone $Z_1$-$Z_4$ can be determined. For example, the previously described calculation of the energy and resource quantity for a tunnel pasteuriser is disclosed in WO 2010/094487 A1.

Then the zone consumptions of all treatment zones $Z_1$-$Z_4$ are summed up in step 223 and output as energy and resource consumption in step 224.

The output degree of pasteurisation or the energy and/or resource consumption is used in optimisation 104, as described in relation to FIG. 1 above, to optimise the target media temperatures.

It goes without saying that features mentioned in the embodiments described above are not limited to these special combinations and are possible in any other combination.

The invention claimed is:

1. A method for operating a tunnel pasteurizer with a plurality of sequentially successive treatment zones, wherein containers with a product packed therein are transported by a conveying device through the treatment zones and are heated with treatment media having different actual media temperatures, are pasteurized, wherein the actual media temperatures are detected by a control unit and compared with target media temperatures, and wherein heating and/or cooling devices are controlled based on the comparison, wherein, during treatment of the containers,
initial values for an optimization are formed from the actual media temperatures of the treatment zones, and
the target media temperatures are determined by a prediction model which determines an expected degree of pasteurization with the optimization such that at least a minimum degree of pasteurization of the containers is achieved, and
wherein an expected energy and/or resource consumption is determined and minimized from the target media temperatures.

2. The method according to claim 1, wherein the optimization takes place simultaneously over at least two of the treatment zones.

3. The method according to claim 1, wherein a momentary degree of pasteurization per container row is determined and then summed up to determine the expected degree of pasteurization.

4. The method according to claim 3, wherein for the treatment zones in each case the momentary degree of pasteurization per container row is determined taking into account a corresponding actual media temperature of the treatment zone and at least one heat transfer parameter of a corresponding treatment medium of the treatment zone to the containers.

5. The method of claim 3, wherein the momentary degree of pasteurization per container row is determined orthogonal to a running direction.

6. The method according to claim 1, wherein during the optimization of the target media temperatures the actual media temperatures are permuted by at least one change value to determine a gradient of the expected degree of pasteurization via the prediction model.

7. The method according to claim 1, wherein the target media temperatures are optimized in such a way that a maximum product temperature is not exceeded.

8. The method according to claim 1, wherein the target media temperatures are optimized in such a way that a maximum temperature jump between two adjacent treatment zones is not exceeded.

9. The method according to claim 1, wherein the target media temperatures are optimized in such a way that a maximum energy and/or resource consumption during the treatment of the containers is not exceeded and/or minimized.

10. The method according to claim 1, wherein the target media temperatures are optimized in such a way that a TAT (time above temperature) value and/or a KP (killing point temperature) value and/or one or more PE (pasteurization units) values are not exceeded.

11. The method of claim 1, wherein after pasteurization, the containers with the product packed therein are then cooled again.

12. A method for operating a tunnel pasteurizer with a plurality of sequentially successive treatment zones, wherein containers with a product packed therein are transported by a conveying device through the treatment zones and are heated with treatment media having different actual media temperatures, are pasteurized, wherein the actual media temperatures are detected by a control unit and compared with target media temperatures, and wherein heating and/or cooling devices are controlled based on the comparison, wherein, during treatment of the containers,
initial values for an optimization are formed from the actual media temperatures of the treatment zones, and
the target media temperatures are determined by a prediction model which determines an expected degree of pasteurization with the optimization such that at least a minimum degree of pasteurization of the containers is achieved, and
wherein an expected energy and/or resource consumption is determined and minimized from the target media temperatures via a second prediction model and compared with the maximum energy and/or resource consumption.

13. The method according to claim 12, wherein the expected energy and/or resource consumption is determined per zone or per row of containers and then summed.

14. The method according to claim 13, wherein for each of the treatment zones a zone consumption and/or a container row consumption is determined taking into account a corresponding media temperature, at least one heat transfer parameter from a corresponding treatment medium to the containers and a heat capacity of the containers.

* * * * *